US012642515B2

(12) United States Patent
Rege et al.

(10) Patent No.: US 12,642,515 B2
(45) Date of Patent: Jun. 2, 2026

(54) MID-INFRARED LASER-ACTIVATED TISSUE SEALING USING BIOMATERIALS

(71) Applicant: Arizona Board of Regents on behalf of Arizona State University, Scottsdale, AZ (US)

(72) Inventors: Kaushal Rege, Gilbert, AZ (US); Ridha Inam, Tempe, AZ (US); Yu Yao, Chandler, AZ (US)

(73) Assignee: Arizona Board of Regents on behalf of Arizona State University, Scottsdale, AZ (US)

( * ) Notice: Subject to any disclaimer, the term of this patent is extended or adjusted under 35 U.S.C. 154(b) by 898 days.

(21) Appl. No.: 17/416,240

(22) PCT Filed: Dec. 19, 2019

(86) PCT No.: PCT/US2019/067463
§ 371 (c)(1),
(2) Date: Jun. 18, 2021

(87) PCT Pub. No.: WO2020/132238
PCT Pub. Date: Jun. 25, 2020

(65) Prior Publication Data
US 2022/0071613 A1 Mar. 10, 2022

Related U.S. Application Data

(60) Provisional application No. 62/781,885, filed on Dec. 19, 2018.

(51) Int. Cl.
*A61B 17/00* (2006.01)
*A61B 18/00* (2006.01)
(Continued)

(52) U.S. Cl.
CPC ........ *A61B 17/00491* (2013.01); *A61L 17/08* (2013.01); *A61L 17/10* (2013.01);
(Continued)

(58) Field of Classification Search
CPC .......... A61B 2017/00508; A61B 18/20; A61B 18/203; A61B 2018/1807;
(Continued)

(56) References Cited

U.S. PATENT DOCUMENTS 5,002,051 A * 3/1991 Dew ................ A61B 17/00491
128/DIG. 22
5,540,677 A * 7/1996 Sinofsky .......... A61B 17/00491
606/8
(Continued)

OTHER PUBLICATIONS

Collagen—Cleveland Clinic (Year: 2024).*
(Continued)

*Primary Examiner* — Darwin P Erezo
(74) *Attorney, Agent, or Firm* — Riverside Law LLP

(57) ABSTRACT

A method of closing an opening in a tissue comprises providing a light absorbing material, introducing the light absorbing material into a tissue opening, and irradiating the light absorbing material with at least one light source so as to increase a temperature of the light absorbing material, causing the tissue edges of the tissue opening adhere to the light absorbing material and/or to each other. A kit comprising a light absorbing material and a light emitting device is also described.

12 Claims, 12 Drawing Sheets

(51) Int. Cl.
   *A61L 17/08*        (2006.01)
   *A61L 17/10*        (2006.01)
(52) U.S. Cl.
   CPC ............... *A61B 2017/00508* (2013.01); *A61B 2018/00452* (2013.01); *A61B 2018/00619* (2013.01); *A61B 2018/0063* (2013.01)
(58) Field of Classification Search
   CPC .... A61B 17/00491; A61B 2018/00452; A61B 2018/00619; A61B 2018/0063; A61B 2018/00494; A61B 2018/00714; A61B 2018/00761; A61B 2018/00791; A61K 41/0052; A61L 17/08; A61L 17/10; A61L 24/001; A61L 24/0015; A61L 24/0031; A61L 24/0042; A61L 24/08; A61L 24/108; A61L 2300/442
   See application file for complete search history.

(56)            References Cited

U.S. PATENT DOCUMENTS

| | | | | |
|---|---|---|---|---|
| 5,662,643 | A | * | 9/1997 | Kung ..................... A61B 18/22 606/8 |
| 5,713,891 | A | * | 2/1998 | Poppas .................. A61B 18/22 606/8 |
| 2003/0040739 | A1 | | 2/2003 | Koop |
| 2004/0030369 | A1 | | 2/2004 | Kubota |
| 2007/0123851 | A1 | * | 5/2007 | Alejandro .......... A61B 18/1492 606/45 |
| 2007/0162121 | A1 | * | 7/2007 | Tarrant ................ A61L 27/3804 623/13.12 |
| 2008/0132467 | A1 | * | 6/2008 | Lauto .................... A61L 24/001 128/898 |
| 2010/0087804 | A1 | * | 4/2010 | Fridman ................ A61B 18/20 606/11 |
| 2011/0124765 | A1 | * | 5/2011 | Yang .................. C08G 65/3322 528/301 |
| 2015/0351767 | A1 | * | 12/2015 | Zoll ................. A61B 17/00491 606/153 |
| 2017/0232157 | A1 | * | 8/2017 | Rege ................... A61B 17/064 606/214 |

OTHER PUBLICATIONS

Illustrated Glossary of Organic Chemistry—Rayon—UCLA (Year: 2024).*

Miles—Thermal Denaturation of Collagen Revisited (Proceedings of the Indian Academy of Sciences—Chemical Sciences) (Year: 1999).*

Abdelgawad, A.M., S.M. Hudson, and O.J. Rojas, Antimicrobial wound dressing nanofiber mats from multicomponent (chitosan/silver-NPs/polyvinyl alcohol) systems. Carbohydr Polym, 2014. 100: p. 166-78.

Annabi, N., et al., Elastic sealants for surgical applications. Eur J Pharm Biopharm, 2015. 95(Pt A): p. 27-39.

Bass, L.S. and M.R. Treat, Laser tissue welding: a comprehensive review of current and future clinical applications. Lasers Surg Med, 1995. 17(4): p. 315-49.

Boonkaew, B., et al., Antimicrobial efficacy of a novel silver hydrogel dressing compared to two common silver burn wound dressings: Acticoat and PolyMem Silver((R)). Burns, 2014. 40(1): p. 89-96.

Bouten, P.J.M., et al., The chemistry of tissue adhesive materials. Progress in Polymer Science, 2014. 39(7): p. 1375-1405.

Lauto, A., Laser-Activated Biomaterials for Tissue Repair, The University of New South Wales, 2005, 173 pages.

Lloyd, J.D., M.J. Marque, and R.F. Kacprowicz, Closure techniques. Emergency Medicine Clinics of North America, 2007. 25(1): p. 73.

Talmor, M., Clifford B. Bleustein, and Dix P. Poppas., laser tissue welding: a biotechnological advance for the future. Archives of facial plastic surgery, 2001. 3: p. 207-213.

Urie et al., "Rapid Soft Tissue Approximation and Repair Using Laser-Activated Silk Nanosealants." Adv. Func. Mat. 2018; 28 (42), 1802874. 11 pages.

Urie, R., et al., Gold Nanorod-Collagen Nanocomposites as Photothermal Nanosolders for Laser Welding of Ruptured Porcine Intestines. ACS Biomaterials Science & Engineering, 2015. 1(9): p. 805-815.

Xie, J., et al., Silver nanoplates: from biological to biomimetic synthesis. ACS Nano, 2007. 1(5): p. 429-39.

* cited by examiner

Cellulose

MID-INFRARED LASER-ACTIVATED TISSUE SEALING USING BIOMATERIALS

CROSS-REFERENCE TO RELATED APPLICATIONS

This application is a U.S. national phase application filed under 35 U.S.C. § 371 claiming benefit to International Patent Application No. PCT/US2019/067463, filed Dec. 19, 2019, which claims priority to U.S. Provisional Patent Application No. 62/781,885, filed Dec. 19, 2018, each of which applications is hereby incorporated herein by reference in its entirety.

STATEMENT REGARDING FEDERALLY SPONSORED RESEARCH OR DEVELOPMENT

This invention was made with government support under R01 EB020690 awarded by the National Institutes of Health. The government has certain rights in the invention.

BACKGROUND

Surgical repair of wounds or openings in body tissues using sutures or other closure means (e.g., staples etc.) are longstanding treatments that have changed very little in recent years. However, sutures and other closure means may not be suitable for use in friable tissue or other tissues or wound types that are difficult to close. Also, suture alternatives, such as staples, nitinol clamps, and surgical adhesives, have not overcome some of the difficulties experienced with sutures, and may have even exacerbated some of the drawbacks of conventional sutures.

Laser tissue welding is a platform technology that has been researched as an alternative to sutures. In laser tissue welding, an exposed chromophore converts laser light to heat to rapidly seal tissue wounds or incisions. With the use of exogenous chromophores in laser tissue welding materials, laser irradiation can be employed at wavelengths of 650-1350 nm; however, tissue absorbance at this wavelength is lowest for light in the near infrared range (700-1000 nm wavelength).

General current state of the art in sutures/other closure methods can include the following types and associated issues. Triclosan-coated sutures still are sutures (e.g., traumatic and must puncture the tissue multiple times) and can have leakage or dehiscence, and the sutures do not integrate with the tissue. Staples require removal; can have leakage, trauma, and inflammation; and may result in greater scarring. Fibrin glue is brittle when cured, may cause problems with sequestering of bacteria, and is not suitable for internal applications. Sealants and adhesives require curing times, which can be long or require a UV light that may be harmful to cells, and typically are used over a sutured closure, and thereby are not standalone products. Albumin solder and other solders for laser tissue welding are liquid systems with inconsistent reproducibility, and they use organic dyes as a chromophore within a liquid, which results in rapid loss of chromophore stability due to photobleaching, and also results in leaching of the chromophore to surrounding tissue, which is not beneficial.

However, wound repair continues to be a surgical necessity, and research into improved wound repair is desirable. Therefore, it would be advantageous to have a system for improving surgical repair of wounds that can overcome the limitations of traditional closure means.

SUMMARY OF THE INVENTION

In one aspect, a method of closing an opening in a tissue comprises providing a light absorbing material, introducing the light absorbing material into a tissue opening, and irradiating the light absorbing material with at least one light source so as to increase a temperature of the light absorbing material, causing the tissue edges of the tissue opening adhere to the light absorbing material and/or to each other. In one embodiment, the method comprises modulating power of the light source to modulate the temperature increase from the light. In one embodiment, the method comprises approximating the tissue portions before, during or after irradiating the light absorbing material. In one embodiment, the method comprises manually holding the tissue portions closer together for a time period between about 1 second and 1 minute. In one embodiment, the tissue opening is in a single tissue. In one embodiment, the tissue opening is between at least two different tissues.

In one embodiment, the temperature increase is sufficient to cause the light absorbing material to interact with the tissue so as to close the opening in the tissue so as to approximate the tissue. In one embodiment, the method comprises forming the tissue opening prior to placing the light absorbing material into the tissue opening. In one embodiment, the at least one light source comprises a laser light. In one embodiment, the at least one light source comprises a mid infrared laser light. In one embodiment, the mid infrared laser light has a wavelength between about 2 microns to about 10 microns.

In one embodiment, the light absorbing material comprises a natural polymer material selected from structural tissue proteins, polysaccharides, extracellular matrix proteins, connective tissue proteins, glycoproteins, glycoaminoglycans, fibrous proteins, protein fibers, or combinations thereof. In one embodiment, the light absorbing material comprises a semi-natural polymer material derived from a natural polymer material selected from structural tissue proteins, polysaccharides, extracellular matrix proteins, connective tissue proteins, glycoproteins, glycoaminoglycans, fibrous proteins, protein fibers, or combinations thereof. In one embodiment, the light absorbing material comprises a synthetic polymer material selected from poly(lactic acid), poly(glycolic acid), poly(lactic-glycolic acid), poly(vinyl alcohol), polyamide, polyurethane, poly(ethylene oxide), polyglyconate, poly(glycolic-caprolactone), polypropylene, polyethylene, poly(hydroxyl acid), polyhydroxyalkanoate, polyanhydride, poly(orthocarbonate), polycarbonate, polyphosphonate, silicones (e.g., polysiloxanes, such as polydimethyulsiloxane (PDMS) or others), or combinations thereof.

In one embodiment, the light absorbing material comprises a crosslinker. In one embodiment, the light absorbing material comprises a photoinitiator. In one embodiment, the light absorbing material comprises a bioactive agent. In one embodiment, the light absorbing material comprises collagen, alginate, chitosan, cellulose, laminin, fibronectin, elastin, hyaluronic acid, fibrin, gelatin, agarose, silk, poly(lactic acid), poly(glycolic acid), poly(lactic-glycolic acid), silicones, poly(vinyl alcohol), polyamide, polyurethane, polyethylene oxide, or combinations thereof.

In one embodiment, the method comprises irradiating the light source for at least 1 minute. In one embodiment, the method comprises irradiating the light source until the light absorbing material increases in temperature to at least 50° C. In one embodiment, the adhered tissue has an ultimate tensile strength of at least 0.25 MPa.

In another aspect, a kit comprises a light absorbing material that generates heat and increases in temperature when it absorbs mid infrared laser light, and a mid infrared laser light emitting device. In one embodiment, the kit further comprises instructions for performing the method as disclosed herein.

BRIEF DESCRIPTION OF THE DRAWINGS

The foregoing purposes and features, as well as other purposes and features, will become apparent with reference to the description and accompanying figures below, which are included to provide an understanding of the invention and constitute a part of the specification, in which like numerals represent like elements, and in which.

DETAILED DESCRIPTION

Figure 1A:
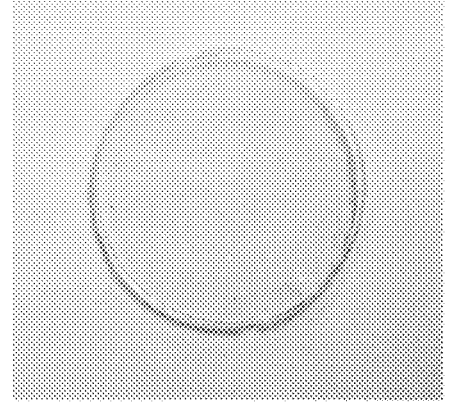
FIG. 1A is a Chitosan—Glutaraldehyde hydrogel.

It is to be understood that the figures and descriptions of the present invention have been simplified to illustrate elements that are relevant for a clear understanding of the present invention, while eliminating, for the purpose of clarity, many other elements found in related systems and methods. Those of ordinary skill in the art may recognize that other elements and/or steps are desirable and/or required in implementing the present invention. However, because such elements and steps are well known in the art, and because they do not facilitate a better understanding of the present invention, a discussion of such elements and steps is not provided herein. The disclosure herein is directed to all such variations and modifications to such elements and methods known to those skilled in the art.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, exemplary methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of 20%, ±10%, +5%, +10%, and ±0.1% from the specified value, as such variations are appropriate.

Throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, 6 and any whole and partial increments therebetween. This applies regardless of the breadth of the range.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

Generally, the present technology includes a light absorbing material that can be placed into a tissue opening (e.g., cut, tear, wound, defect, or other) and then radiated with light from a light source so as to absorb the light and increase the temperature to a temperature that is sufficient to cause the material to interact with the tissue so as to close the opening in the tissue so as to approximate the tissue. In different embodiments, a method may include irradiating the light from the light source until the light absorbing material increases in temperature to at least 50° C., at least 60° C., at least 65° C., at least 70° C., at least 75° C., or any value between these values. The light absorbing material can provide an improvement over other wound closure techniques and materials or at least provide suitable wound closure. The light absorbing material may be used with or without sutures, staples, clamps and/or tissue glues (e.g., cyanoacrylate based glues, such as Dermabond). Preferably, the light absorbing material can be used without sutures, staples, clamps, tissue glues, and/or any other structural element with the light absorbing material. In some aspects, the light absorbing material can be used to approximate tissues prior to using sutures and/or staples. In some aspects, the light absorbing material can be used in place of a tissue glue. A tissue opening may in some embodiments be an opening in a single tissue, or in two or more different tissues.

The light absorbing material can be placed into a tissue opening and then irradiated with light so as to approximate tissue edges together, such as in surgery, wound healing or other. The light absorbing material when irradiated with light can be used to approximate tissue edges to provide improved tissue mechanical strength, reduce infection, reduce dehiscence, reduce wound leakage, and reduce acute inflammation. In some embodiments, a method may comprise forming the tissue opening prior to placing the light absorbing material into the tissue opening.

While the light absorbing material can absorb any type of light to increase the temperature thereof, laser light can be preferred. Additionally, laser-activated tissue sealing is known, and thereby the light absorbing material can be used in laser tissue sealing where the laser can be absorbed by the light absorbing material to cause a temperature increase. The laser light energy can be used to increase the temperature of the light absorbing material and the tissue interface surfaces in contact with the light absorbing material. Thereby, the light absorbing material when irradiated with a laser can facilitate tissue fusion with the light absorbing material and facilitate tissue-tissue fusion in areas around the light absorbing material.

Traditionally, light-absorbing chromophores and nanoparticles (e.g. gold nanorods) have been employed for converting near infrared (NIR) laser light to heat, resulting in the photothermal fusion of the sealant biomaterial with soft tissues. In certain embodiments, the light absorbing material can be used without any chromophores or nanoparticles.

Now, it has been found that a light absorbing material, such as the natural polymers, semi-natural polymers or synthetic polymers with or without a crosslinker, such as the light absorbing materials described herein, that absorbs light, whether infrared, visible or ultraviolet, can be used as described herein to approximate tissue edges and close an opening in a tissue. However, it can be preferable that the light source is laser light, more preferably laser infrared light, and most preferably mid infrared light. In some embodiments, a mid infrared laser light may have a wavelength between about 2 microns to about 10 microns, or between about 4 microns to about 8 microns, or between about 5 microns to about 7 microns, or between about 6 microns to about 7 microns.

The light absorbing material can be used for sealing tissues without the need for chromophores or nanoparticles by using mid infrared (e.g., midIR) laser light. It has been found that some biomaterials absorb midIR wavelengths of light (e.g., 2-10 micron wavelengths). It was found that absorption of midIR laser light energy results in an increase in temperature in the light absorbing materials, which can, in turn, promote adhesion of the light absorbing material to the tissues and promote tissue surface or edge approximation and/or sealing.

In some embodiments, the absorption of midIR laser light by several different biomaterials (e.g. silk, cellulose, etc.) was confirmed to result in a rise in local temperature at different laser powers. Optimal operating conditions were employed for midIR based photothermal sealing of incised and/or ruptured tissue ex vivo and in different skin surgical models in live mice. It was found that the use of the light absorbing material treated with midIR laser light resulted in recovered biomechanical properties of the tissue, and thereby the treated tissue was about as good as un-ruptured or uncut tissue. For example, recovery of mechanical properties included recovered tensile strength and recovered maximum strain. In some embodiments, treated tissue could have a resultant ultimate tensile strength of at least 0.25 MPa, at least 0.5 MPa, at least 0.75 MPa, at least 1 MPa, at least 1.5 MPa, at least 2 MPa, at least 3 MPa, at least 4 MPa, at least 5 MPa, at least 10 MPa, or any value between these ranges. The recovered mechanical properties, in concert with histopathology analyses, determined the efficacy of the seal with the light absorbing material treated with midIR laser light. The effect of midIR laser light on cell and tissue viability was also determined. The results demonstrated that midIR lasers can be used for rapid sealing of soft tissues using conventional biomaterials that perform as light absorbing materials without the need for chromophores or nanoparticles. The lack of chromophores or nanoparticles can provide a significant advantage for moving this treatment into the real clinical world to treat real patients.

Various light absorbing materials can be inserted into a tissue opening prior to being treated with midIR laser light for tissue sealing, anastomosis, wound repair, and/or other tissue healing. The light absorbing material can be selected based on a function as both a photothermal convertor as well as a sealant. In some embodiments, the light absorbing material may comprise a natural material. In some embodiments, the light absorbing material may comprise a natural polymer material, or a semi-natural polymer material as disclosed elsewhere herein. In some aspects, the light absorbing materials can be pristine materials or pristine biomaterials (e.g., natural, semi-natural, or synthetic) without having any chromophores and/or nanoparticles. The light absorbing materials can be biocompatible to obviate any issues related to toxicity. The use of pristine biomaterials can also facilitate localization of the heat from the midIR laser light heating the biomaterial, which has the potential to reduce thermal damage to tissue outside or surrounding the tissue opening. As such, the combination of the light absorbing material and midIR laser light can reduce unwanted collateral tissue damage that may occur with other materials, such as those with chromophores and/or nanoparticles. Thus, the use of pristine biomaterials without chromophores and/or nanoparticles in tissue openings that are treated with midIR light can result in improved cosmesis, particularly on visible areas of the body because of the translucent nature of the light absorbing materials. As a result, the subject of the tissue approximation treatment can have improved cosmetics compared to traditional tissue approximation techniques, such as staples, sutures, or the like. In some embodiments, the light absorbing material comprises a bioactive agent.

In some embodiments, the midIR laser light treatment of the light absorbing material can avoid: granuloma formation; inflammatory response; sub-optimal approximation; nerve damage; capillary damage; ischemia; body fluid leakage; or other problems.

In some embodiments, the midIR laser light treatment of the light absorbing material can replace tissue sealants. Common tissue sealants are insufficient for wet and highly dynamic environments. Common tissue sealants often suffer from low adhesion, low elasticity and low stiffness and typically result in poor mechanical strength. For example, the midIR laser light treatment of the light absorbing material can replace cyanoacrylates and fibrin glues.

The light absorbing material can be used in place of traditional laser tissue sealing or welding.

In some embodiments, a tissue closure composition that absorbs light, such as mid infrared (midIR) laser or other light, can be adapted for use in order to close an opening in a tissue. Such a composition can include a biocompatible material that is configured as a light absorbing material that is responsive to mid infrared laser light so as to absorb the light to cause heating of the light absorbing material. In one aspect, the light absorbing material is a natural or synthetic polymer that is biodegradable and/or bioabsorbable while being capable of absorbing light. By being responsive to and absorbing light, the light absorbing material heats up to a sufficient temperature to allow for bonding with tissues in contact with the light absorbing material.

In some embodiments, the light absorbing material includes a biocompatible natural and/or semi-natural and/or synthetic polymer.

Some examples of natural polymers that can be configured as light absorbing materials can include: structural tissue proteins, such as collagen or other structural proteins from skin or other connective tissues; polysaccharides, such as alginate, chitosan, chitin, agarose, or cellulose; extracellular matrix or connective tissue proteins, such as laminin or elastin; glycoproteins, such as fibronectin; glycosaminoglycans or any type, such as hyaluronic acid, whether sulfated or non-sulfated; fibrous proteins, such as fibrin, whether globular or non-globular; chemically modified structural tissue proteins, such as gelatin, which is from hydrolyzed collagen; or a protein fiber, such as silk; or combinations thereof.

In some embodiments, any type of collagen can be used for the light absorbing material. For Example, the collagen can include: Type I collagen from skin, tendon, vasculature, organs, or bone; Type II collagen from cartilage; Type III collagen that is reticulate, such as from reticular fibers; Type IV collagen from basal lamina; Type V collagen from cell surfaces, hair, and placenta. The collagen can be completely natural or semi-natural if chemically processed or otherwise derivatized.

In some embodiments, any type of polysaccharide can be used for the light absorbing material. There are many different polysaccharides that can be used in the present technology. The substances can include polymeric carbohydrates that include chains of monosaccharides coupled through glycosidic linkages, and which may give monosaccharides or oligosaccharides upon hydrolysis or other cleavage. Example polysaccharides can include alginate, chitosan, chitin, agarose, cellulose; cellulose acetate, celluloid, nitrocellulose, starch, amylose, pectin, amylopectin, glycogen, callose, laminarin, chrysolaminarin, xylan, arabinoxylan, mannan, fucoidan, and galactomannan, combinations thereof, or others.

In some embodiments, the glycoprotein can include proteins with oligosaccharide chains (e.g., glycans) attached to amino acid side-chains. Examples can include fibronectin, mucins, immunoglobulins, gonadotropins, miraculin, or others.

In some embodiments, the glycosaminoglycans can include chondroitin sulfate, dermatin sulfate, keratin sulfate, heparin, heparin sulfate, hyaluronan, and others, In some embodiments, the fibrous proteins can include fibrin, actin, Arp2/3, coronin, dystrphin, elastin, F-spondin, fibronectin, keratin, myosin, nebulin, pikachurin, spectrin, tau, tinin, tropomyosin, tubulin, combinations thereof, or others.

In some embodiments, the structural fiber can be silk from any origin. The silk may be from any insect or arachnid or arthropod. Some examples include silk worms, webspinners, raspy crickets, bees, wasps, ants, silverfish, mayflies, *thrips*, leafhoppers, beetles, lacewings, fleas, flies, midges, or others.

In some embodiments, the light absorbing material can be a semi-natural polymer, which can be derived from any natural polymer, such as those described herein or otherwise known. For example, a semi-natural polymer can be obtained by chemically modifying or otherwise derivatizing a natural polymer. Semi-natural polymers can also include natural polymers, whether natural or chemically modified, having other substances contained therein. The substances can be fillers, crosslinkers, or other materials. In some aspects, the semi-natural polymer can include a light absorbing substance, which is not a light responsive particle (gold) or a pigment or dye.

In some embodiments, the light absorbing material can be a synthetic polymer. Examples of synthetic polymers that can be used as light absorbing materials can include poly (lactic acid), poly(glycolic acid), poly(lactic-glycolic acid), poly(vinyl alcohol), polyamide, polyurethane, poly(ethylene oxide), polyglyconate, poly(glycolic-caprolactone), polypropylene, polyethylene, poly(hydroxyl acid), polyhydroxyalkanoate, polyanhydride, poly(orthocarbonate), polycarbonate, polyphosphonate, silicones (e.g., polysiloxanes, such as polydimethyulsiloxane (PDMS) or others), combinations thereof, or others. The synthetic polymer can be biodegradable or biostable. "Biostable" denotes a high chemical stability of a compound in an aqueous environment, which is similar to the environment, found in the human body, such as, by way of example, and not limitation, phosphate buffered saline (pH 7.2). "Biodegradable polymer" denotes those polymers that degrade or hydrolyze inside the human or animal body without producing harmful degradation products. Poly(lactic acid) poly(lactide) (PLA) is a term used for a polymer which is made from lactide or lactic acid. Similarly, PGA is a term used for polyglycolic acid or polyglycolate. Such polymers are generally referred to as polylactones or polyhydroxyacids.

In some embodiments, the light absorbing material may be configured as a hydrogel. A "hydrogel" refers to a semisolid composition constituting a substantial amount of water, and in which polymers or mixtures thereof are dissolved or dispersed. The hydrogels may be physically or chemically crosslinked.

In some embodiments, the light absorbing material may include a crosslinker. For example, the crosslinker can be included with a natural polymer, semi-natural polymer, or synthetic polymer. The crosslinker can crosslink the material. "Crosslink" is defined as understood by those skilled in polymer chemistry art. In general, cross-linking refers to the method of forming covalent bonds or crosslinks between polymeric/macromolecular molecules. The crosslinking process also generally refers to a fixation process which stabilizes the tissue by making the tissue less antigenic and thus less susceptible to enzymatic degradation. A "crosslinking agent" is defined as a compound capable of forming the crosslinking. For example, glutaraldehyde is generally known in the art as a crosslinking agent for the tissue.

In some embodiments, the crosslinker can include poly (ethylene glycol) diglycidyl ether, glycerol diglycidyl ether, 1,4-butanediol diglycidyl ether, ethylene glycol glycidyl ether, polypropylene glycol diglycidyl ether, combinations thereof, or others.

In some instances, the crosslinker may be in the light absorbing material prior to actually crosslinking. Then, the crosslinker can be activated to crosslink the composition. Such crosslinking can occur prior to implanting in a tissue opening, during implanting into a tissue opening, or after implanting in the tissue opening.

In some instances, the light absorbing material can be used by being placed in a tissue opening without being crosslinked and then being crosslinked in situ. As such, a crosslinking initiator, such as a photoinitiator, can be included in the uncrosslinked light absorbing material. Then, after installation in the tissue opening, the photoinitiator can be activated for crosslinking, which can be the same light (e.g., mid infrared) or a different light from the light that is used for causing the light absorbing material to heat and seal the tissue to close the tissue opening.

As used herein, a mid infrared (midIR) laser light can have a wavelength of from about 2-10 microns, 4-8 microns, 5-7 microns, or about 6 microns. Although embodiments are described herein using a midIR laser light as a light source, in other embodiments any light source may be used, including but not limited to a light emitting diode (LED), a lamp, a focused light source, a diffuse light source, or any other source of light capable of activating a light absorbing material used herein.

The light absorbing materials can be liquid, gels, hydrogels, pastes, or films when applied to the tissue opening, or after being processed in situ. The components of the polymeric films are composed of but not limited to the following: natural polymers, such as collagen, alginate, chitosan, cellulose, laminin, fibronectin, elastin, hyaluronic acid, fibrin, gelatin, agarose, silk, or combinations thereof; synthetic polymers, such as poly(lactic acid), poly(glycolic acid), poly(lactic-glycolic acid), silicones, poly(vinyl alcohol), polyamide, polyurethane, polyethylene oxide, or combinations thereof; and optionally crosslinkers, such as poly (ethylene glycol) diglycidyl ether, glycerol diglycidyl ether, 1,4-butanediol diglycidyl ether, ethylene glycol glycidyl ether, polypropylene glycol diglycidyl ether, or combinations thereof. Chemical modifications and derivations can also be made to the above materials using chemical moieties as substituents to further enhance the absorption in the midIR range resulting in further efficacy of sealing and tissue repair.

Accordingly midIR activation of biomaterials can be used for sealing, closing or approximation of tissue for repair and healing. Several biomaterials including silk, alginate, chitosan and collagen have been shown to absorb the midIR laser light resulting in an increase in local temperature and rapid sealing with intestinal and/or skin tissue.

In one embodiment, a method of promoting wound healing can include: providing a light absorbing material of one of the embodiments; introducing the light absorbing material into a tissue opening; and stimulating light absorbing material with at least one light so as to cause the light absorbing material to increase in temperature so that the tissue portions of the tissue opening (e.g., wound) adhere to each other and/or to the light absorbing material in response to the increased temperature. In some aspects, the temperature increase from the light can cause approximating of tissue portions of a wound with the light absorbing material. In some embodiments, a method of the invention may include moving one or more tissue portions closer together, either manually or via light applied to the light absorbing material. In some embodiments, a method may include holding one or more tissue portions closer together either by hand or with an instrument for a period of time between 1 second and 10 minutes, or between 1 second and 5 minutes, or between 1 second and 1 minute, or between 1 second and 10 seconds.

In one aspect, the method includes irradiating the light absorbing material to generate heat that causes tissue components of the tissue portions of the tissue opening to interdigitate. In one aspect, the method includes irradiating the light absorbing material to cause the tissue portions to weld and seal the wound. In various embodiments, a method may include irradiating the light for at least 1 minute, at least 5 minutes, at least 10 minutes, at least 15 minutes, or for any duration in the range of one second to 20 minutes, one second to 30 minutes, or one second to 60 minutes. In one aspect, the method includes eluting a biologically active agent (e.g., drug, such as antibiotic or wound healing drug) from the light absorbing material into the wound. In one aspect, the method includes causing tissue integration of the tissue portions. In one aspect, the light absorbing material can be in the form of a liquid, gel, hydrogel, paste, or film before, during, or after application to a tissue opening or other wound in a tissue.

These light absorbing materials can provide improved performance in facilitating repair of the wounded tissue due to their dual properties of mechanical strength and stimulus triggered tissue integration by light absorption. By integrating with the surrounding tissues, these light absorbing materials (e.g., biodegradable) generate a homogenous weld/seal across the injury. Alternatively, when the light absorbing materials (e.g., biostable staple) does not integrate with the tissue, the tissue on each tissue portion can integrate together. The resultant healed wound is more stable and is less prone to wound dehiscence and leakage (or other problems) than obtained from other wound healing techniques.

The light absorbing materials can generate heat when subjected to the light stimulus in order to initiate tissue welding and in some instances cause integration via heat generation, which leads to protein interdigitation or chemical reaction with the tissue. The light absorbing materials can provide dual benefits that include accurate tissue approximation followed by tissue welding and integration, which can increase mechanical stability of the wound closure that can lead to rapid healing. Also, the methods of use can include modulating the power or intensity or time of application of the light stimulus to modulate the heat generation. The modulation of the light stimulus can be conducted during the surgical procedure, where the temperature of the wound and/or light absorbing materials can be monitored with a temperature monitoring device, and the application of the light stimulus can be modulated in order to modulate the temperature.

Additionally, the use of the light stimulus can allow for accurate and precise control of the tissue integration process to avoid any unnecessary inflammation, fluid influx, and neutrophil extravasation that could compromise the weld strength. The protocol can include modulating the light stimulus to reduce the action if any inflammation, fluid influx, and neutrophil extravasation is observed.

In one embodiment, the light absorbing material may also include a biologically active agent, such as a drug. In one example, the light absorbing material can include an antimicrobial (e.g., antibiotic) that can inhibit infections in the wound. Such active agents can enhance the healing. As such, the light absorbing material can be configured to allow drug elution from the light absorbing material before, during, and after tissue integration from the light stimulus, which can provide for faster healing of the wound tissue.

The light absorbing material can provide sufficient support to properly seal the torn/injured soft tissues after surgery or accident. The light absorbing material can be used to bring two tissue ends together before being simulated to promote improved tissue sealing and healing. The light absorbing material can inhibit tissue dehiscence and leakage of contents into the surroundings from a wound or tissue opening.

In some embodiments, the light absorbing material can be specifically devoid of a stimuli responsive particle, such as being devoid of a gold particle, or being devoid of a light absorbing particle.

In some embodiments, the light absorbing material can be devoid of a colorant, which can be any substance that imparts a color that is not present in the natural, semi-natural, or synthetic polymer. In some aspects, the light absorbing material may be devoid of a dye, such as being devoid of a dye that absorbs mid infrared light. In some aspects, the light absorbing material may be devoid of a pigment, such as being devoid of a pigment that absorbs mid infrared light. Herein, dyes are defined as being smaller or finer than pigments, where dyes are often dissolvable in a liquid. On the other hand, a pigment is a particle often larger than a dye particle, where pigments can be characterized as being capable of being suspended in a liquid without dissolving.

In some embodiments, a kit of the present disclosure may comprise a light source as contemplated herein, for example a mid infrared light emitting device, for example a mid infrared laser, and a light absorbing material that generates heat and increases in temperature when it absorbs light, for example light emitted by the light emitting device. A kit may further include instructions for performing any method described herein.

Experimental Examples

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the system and method of the present invention. The following working examples therefore, specifically point out the exemplary embodiments of the present invention, and are not to be construed as limiting in any way the remainder of the disclosure.

The following provides a description of procedures for synthesizing polymeric hydrogels to be used in mid-IR laser tissue sealing.

Chitosan flakes (e.g., low molecular weight, >75% deacetylated), sodium carboxymethyl cellulose, and Alginic acid sodium salt were purchased from Sigma-Aldrich, and silk polymer used in this study was extracted from *Bombyx mori* Cocoons based on a well-known protocol. Chitosan was dissolved in a 1.0 wt % aqueous acetic acid solution at a concentration of 2.0 wt %. Glutaraldehyde was diluted in 0.05% and was added to the chitosan solution in a 1 w/v %. Silk, cellulose, and alginate were dissolved in nano-pure water at the concentration of 2.0 wt %. The 2.0 wt % polymeric solutions were cast in glass bottom well plates at room temperature for 24 h. Then the cast films were rinsed with nanopore water and dried at room temperature for 24 h to evaporate the solvent thoroughly and obtain the polymeric films.

FIG. 1A shows a chitosan-glutaraldehyde hydrogel, which is an example of a light absorbing material.

Figure 1B:
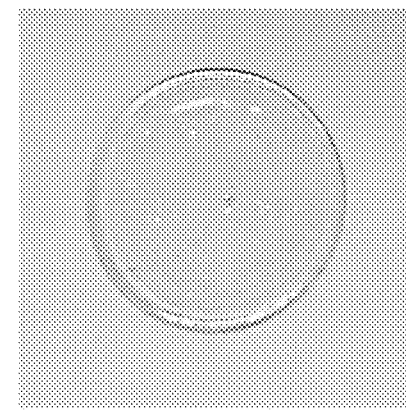
FIG. 1B is a Silk—Glycerol hydrogel.

FIG. 1B shows a silk-glycerol hydrogel, which is an example of a light absorbing material.

Figure 1C:
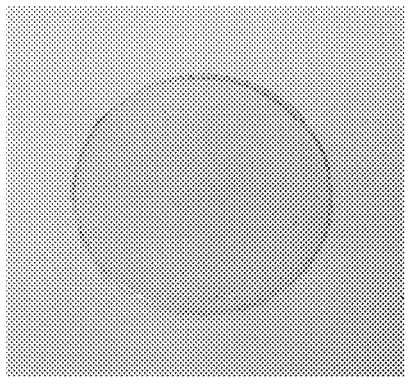
FIG. 1C is an Alginate—Glycerol hydrogel.

FIG. 1C shows an alginate-glycerol hydrogel, which is an example of a light absorbing material.

Figure 1D:
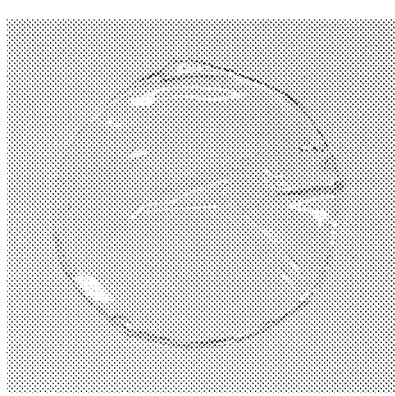
FIG. 1D is a Cellulose—Glycerol hydrogel.

FIG. 1D shows a cellulose-glycerol hydrogel, which is an example of a light absorbing material.

Figure 2:
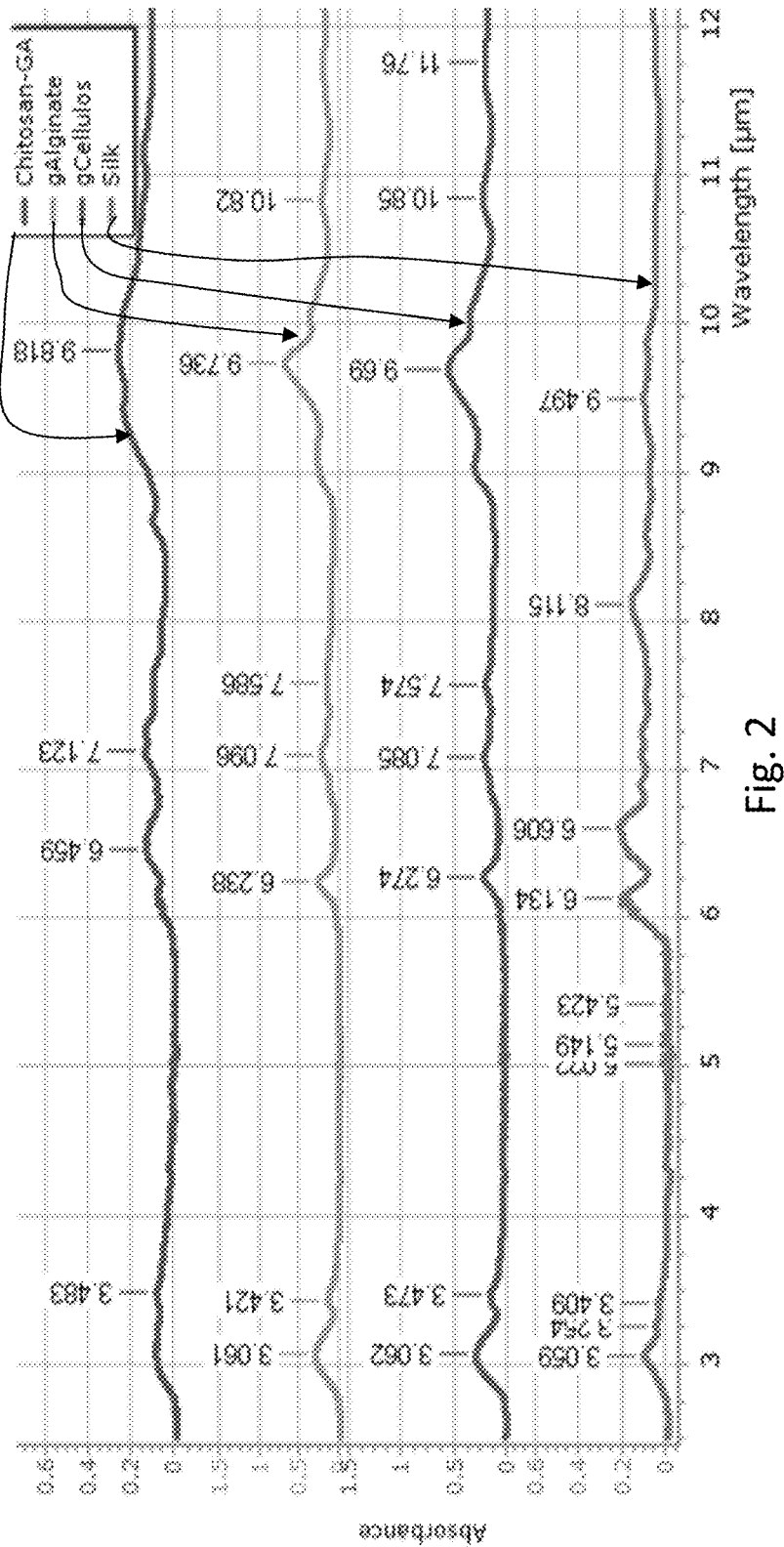
FIG. 2 is an FTIR analysis of different hydrogels used in the study and their absorption at 6.5 microns (1532 cm-1)

FIG. 2 shows FTIR analysis of different hydrogels used in the study and their absorption at 6.5 microns (1532 cm-1).

The films were tested using ex vivo porcine intestine and mouse skin to seal the surgical wound created on them. The films were placed on the tissue and were exposed to the midIR laser beam corresponding to the maximum absorbance (e.g., 6.5 microns wavelength) for a specific duration of time (1-5 minutes). The temperature was monitored during laser exposure. Elevation of the polymeric film and the tissue temperatures result in tissue-matrix integration and tissue sealing of porcine intestine and mice skin.

Observations

The photothermal response of the hydrogels were studied using a Quantum Cascade Laser (MIRcat-QT™ Mid-IR Laser) with wavelength tuned to 6.5 μm, used at power densities of 1.05 W/cm$^2$. In each power, the laser was on for 30 seconds and off for another 30 seconds. The cycle repeated two more times.

Figure 3A:
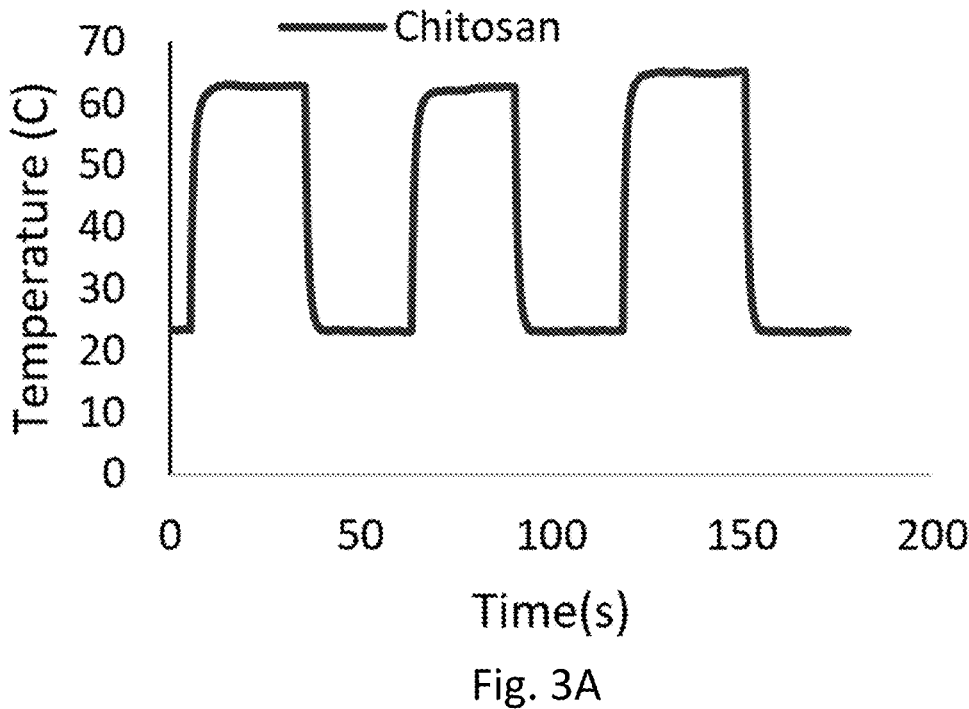
FIGS. 3A-3D are Photothermal behavior of Different polymeric films under 1.19 W/cm$^2$ power density.
Figure 3B:
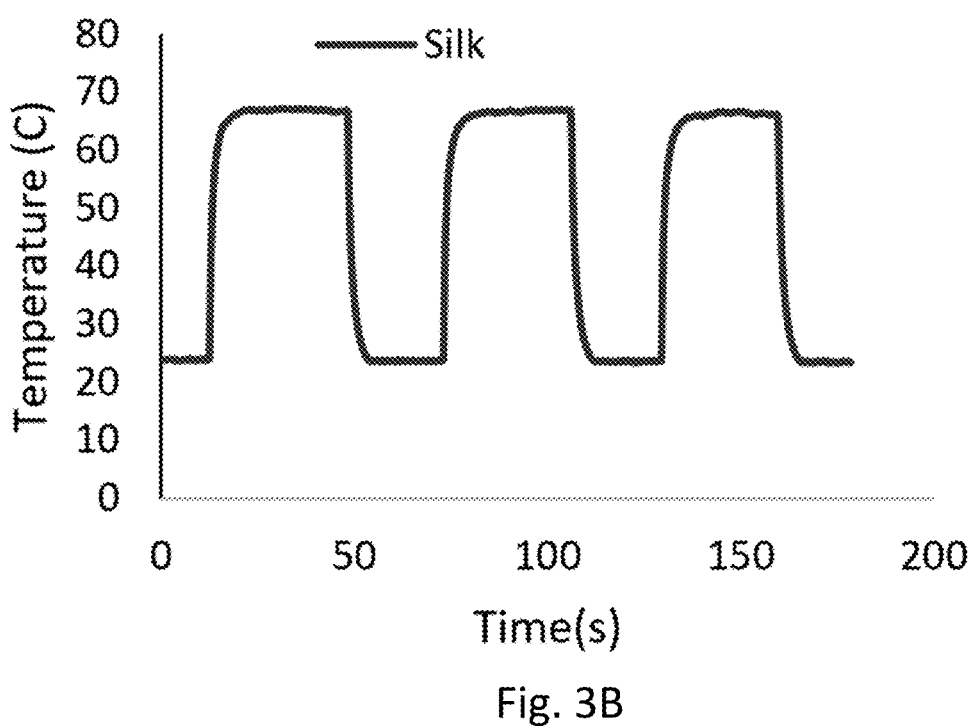
Figure 3C:
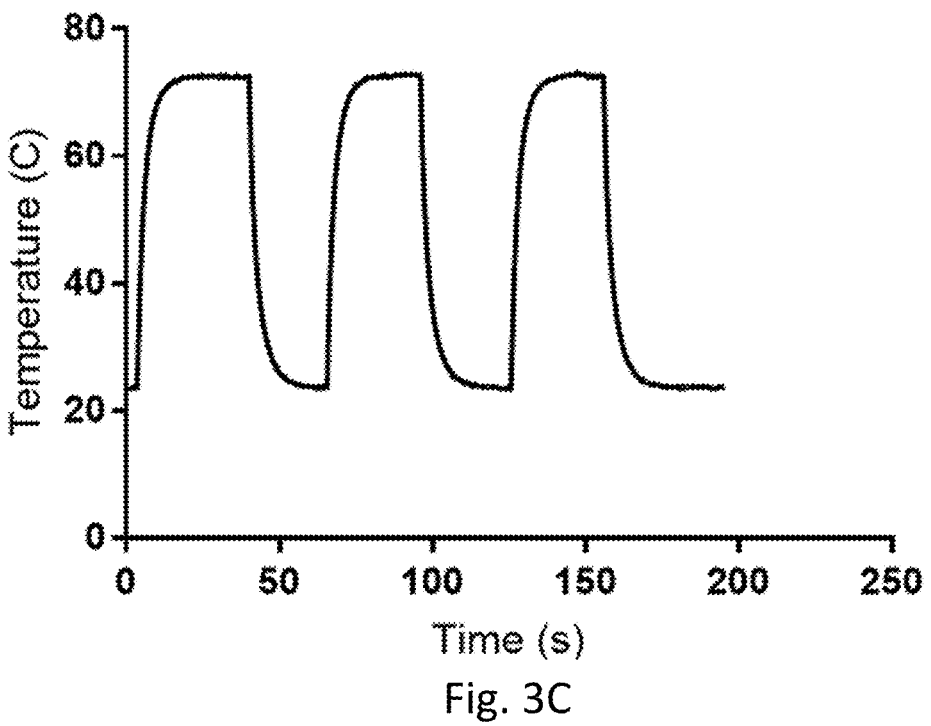
Figure 3D:
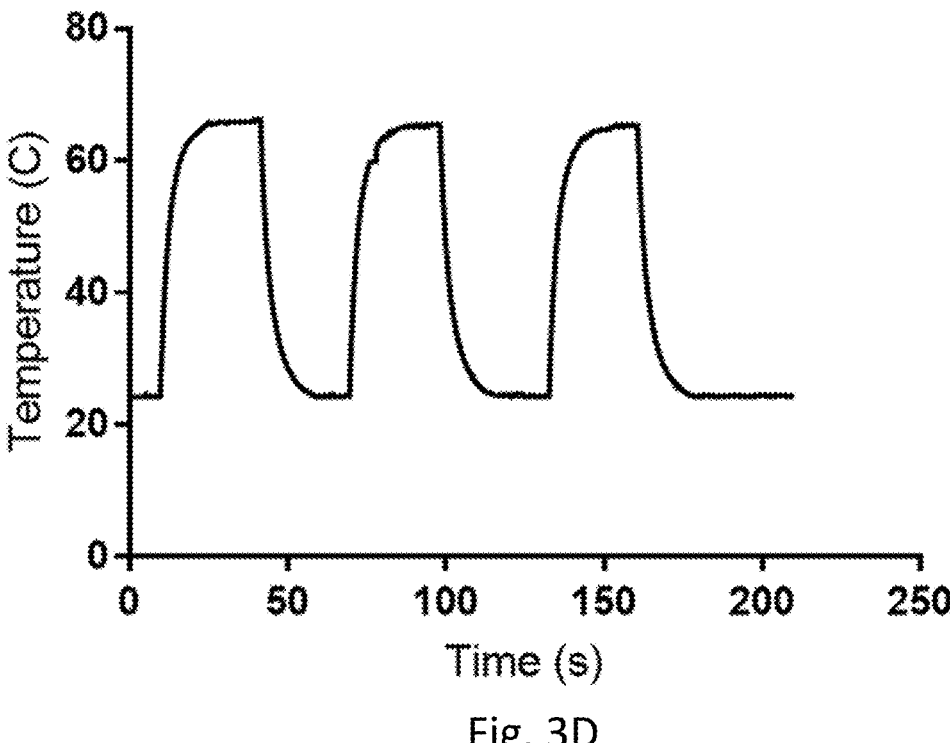

FIGS. 3A-3D show the heat response upon applying the laser beam. FIG. 3A is chitosan. FIG. 3B is silk. FIG. 3C is alginate. FIG. 3D is cellulose. The film temperature can reach 70° C. in the first 10 seconds after it is exposed to the laser.

Figure 4:
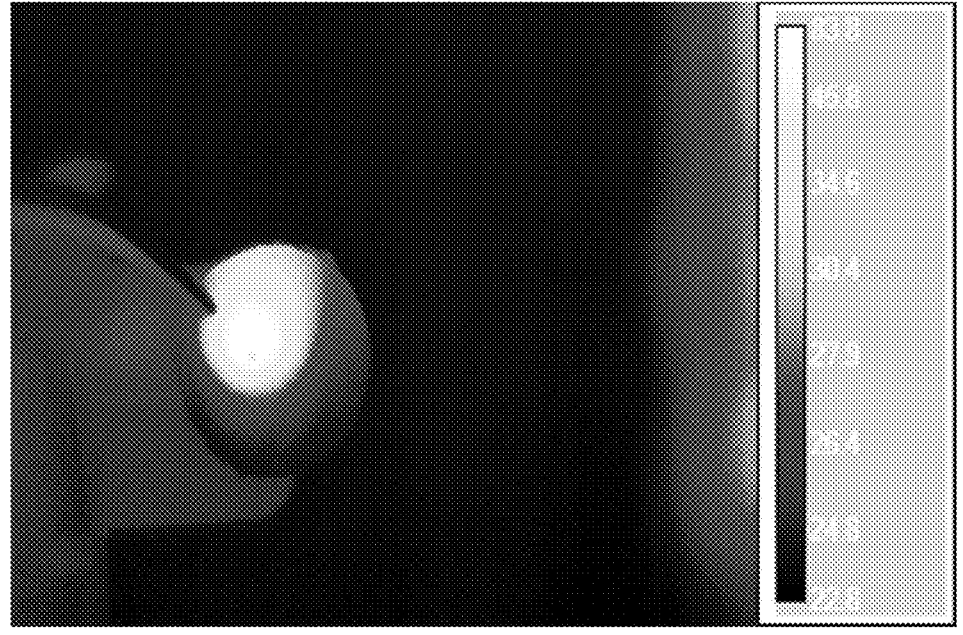
FIG. 4 is an example of photothermal images of polymeric film under mid-IR laser exposure.

FIG. 4 shows a photothermal image of a polymeric film under midIR laser exposure.

Porcine intestine sections of length 7-10 cm, and width of 1.4 cm were prepared with a 10 mm through incision to the wall. The hydrogel sample was placed over the top of the incision site and was subjected to mid-infrared laser at the power density of 1.47 W/cm$^2$ for 3 minutes.

For the adhesion testing, the ultimate tensile strength of the tissue under tension, maximum strain and modulus of toughness were measured using TA.XTPlus Texture Analyzer. Each end of the rectangular tissue sample was held by clamps and pulled apart at a rate of 1 mm/s until the tissue reached failure. The maximum force (F) and area of the tissue sample (A) determined the ultimate tensile strength ($\sigma$, kPa) of the welded tissue ($\sigma$=F/A). The total area under the strain-stress curve up to failure was considered as modulus of toughness. Intact intestine (no central incision) was also tested to establish an ultimate tensile strength for native tissue.

Figure 5:
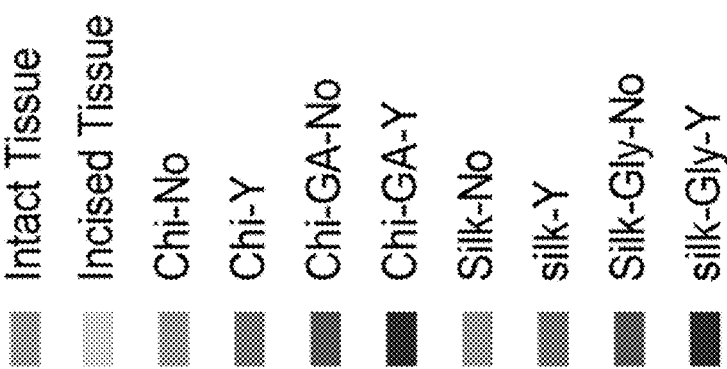
FIG. 5 is a graph of ultimate tensile strength for chitosan, chitosan-Ga, silk, silk-Gly hydrogels. "No" states that the hydrogels were not exposed to mid-infrared laser. "Y" states that the hydrogels were laser treated (n=3 for each condition)
Figure 5:
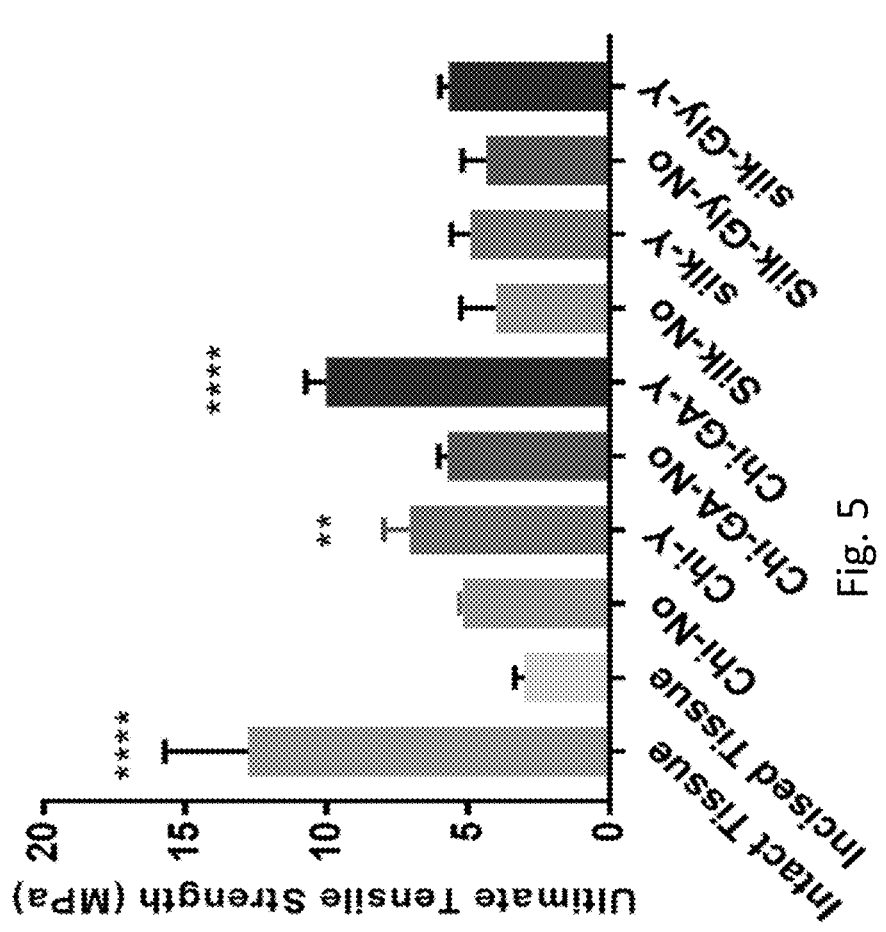

FIG. 5 shows the ultimate tensile strength for chitosan, chitosan-Ga, silk, and silk-Gly hydrogels. "No" states that the hydrogels were not exposed to mid-infrared laser. "Y" states that the hydrogels were laser treated (n=3 for each condition).

Figure 6A:
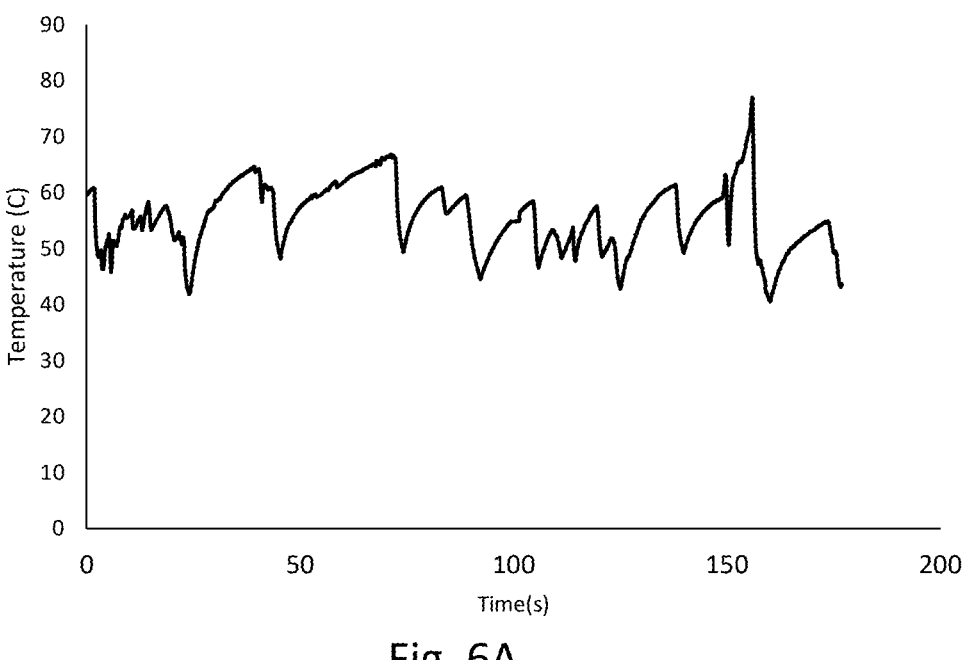
FIG. 6A is a temperature elevation monitored during laser tissue sealing.

FIG. 6A shows the temperature elevation monitored during laser tissue sealing with the light absorbing material, chitosan-glutaraldehyde hydrogel.

Figure 6B:
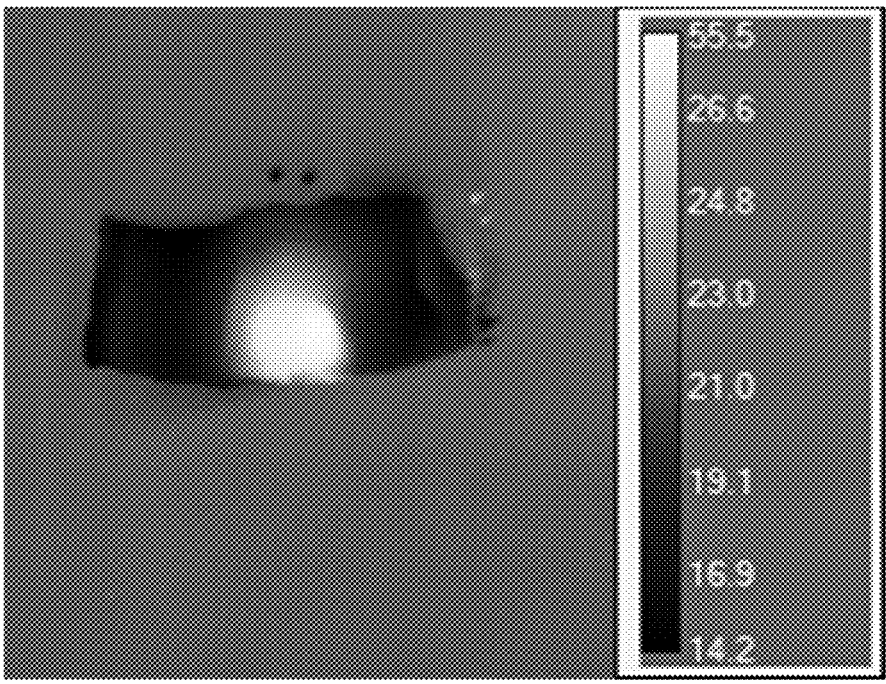
FIG. 6B is a set of photothermal images during laser tissue sealing.

FIG. 6B shows the photothermal image during laser tissue sealing with the light absorbing material, chitosan-glutaraldehyde hydrogel.

BALB/c mice cadavers were used for ex-vivo study using dorsal skin incision model. The back of each mouse was shaved and one 1-cm full skin incision was made on the back of the mouse with at least 1 cm distance. The polymeric films were cut and wetted by 1-2 drops of water and were placed on the incision. The film covered incision was subjected to 6.5 microns laser beam for 2 minutes. The surface temperature, which was recorded by IR camera, was kept between 60–75° C. As shown in FIGS. 3A-3D, the polymeric film triggered by laser sealed the skin incision.

The light absorbing materials were used with the mouse model as described herein. Images were taken that show that the light absorbing material was indeed capable of being used as described herein. For cadaver models, the skin was shown to remain attached to the film formed by midIR laser treating the light absorbing material, even after being peeled from the cadaver.

For live mice, the light absorbing materials once treated with midIR laser light was shown to be suitable for wound healing.

Figure 7A:
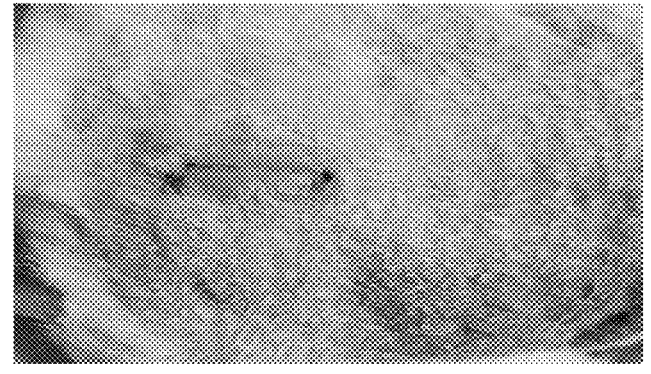
FIGS. 7A-7B show silk on mouse skin after laser treatment.
Figure 7B:
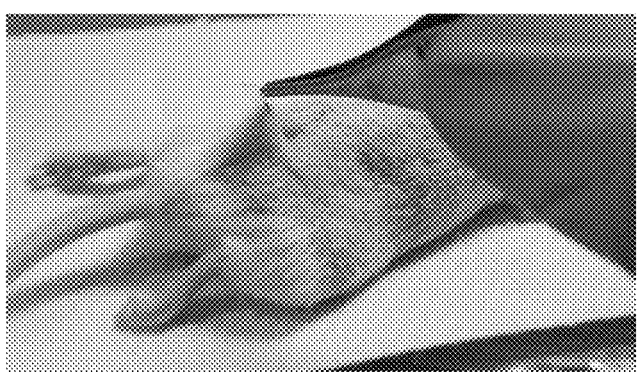
Figure 8A:
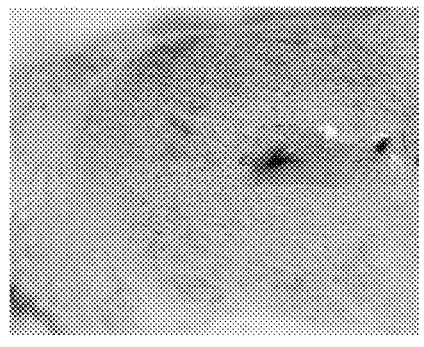
FIGS. 8A-8B show cellulose on mouse skin after laser treatment.
Figure 8B:
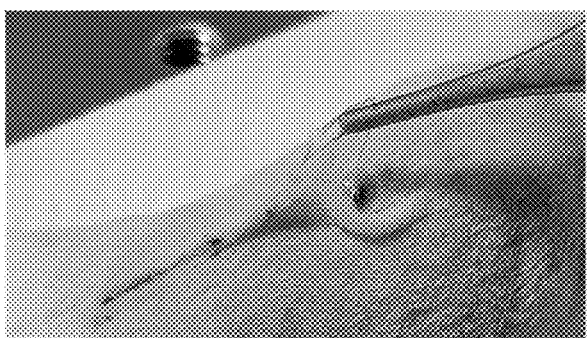

FIG. 7A shows the silk light absorbing material after laser treatment. FIG. 7B shows the silk material adheres to the skin quite strongly.

FIGS. 1A-8B show cellulose on mouse skin after laser treatment.

While not show, the silk and cellulose retained some skin after being peeled from the mouse.

Figures 9A, 9B, 9C, 9D:
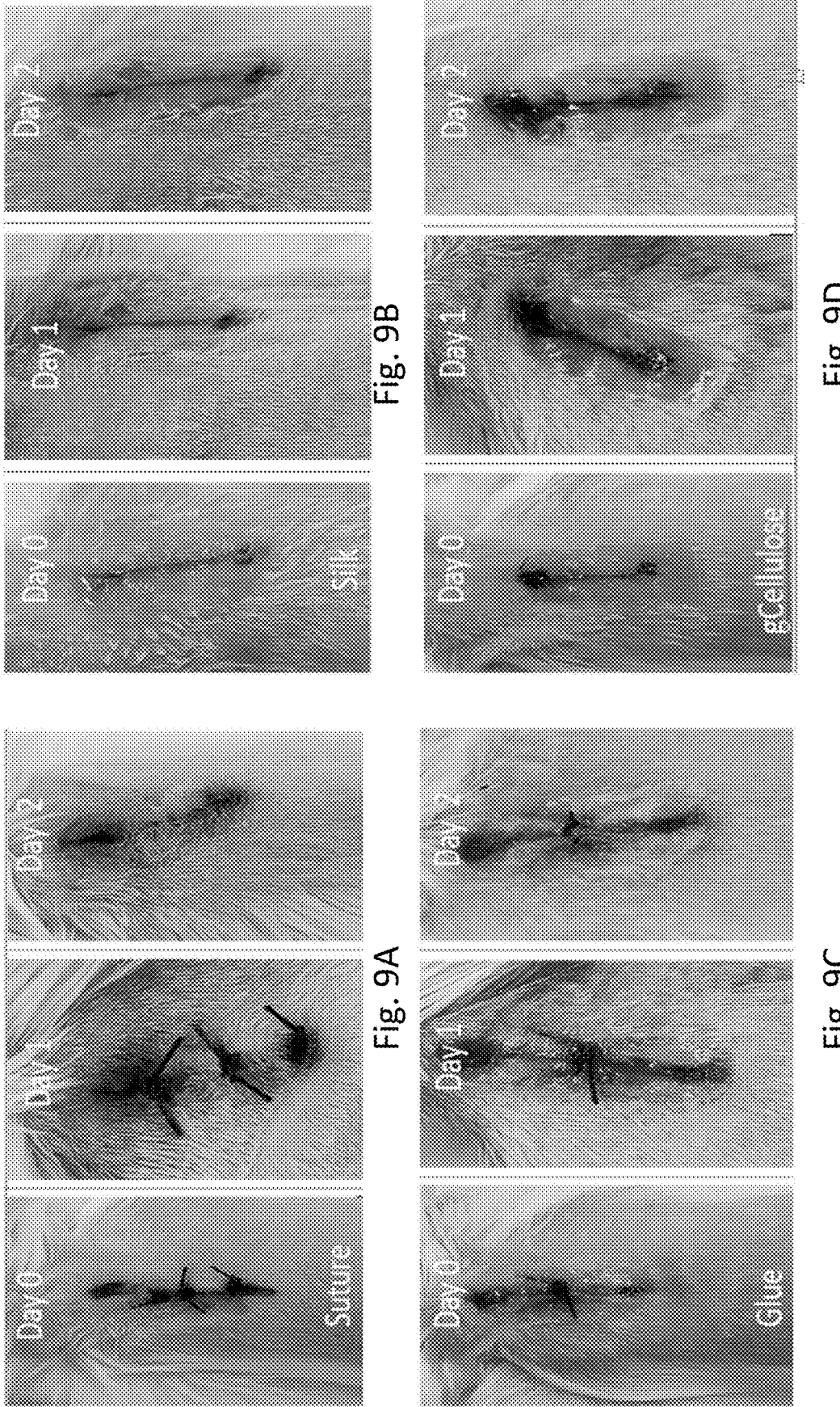
FIGS. 9A-9D show healing of incised skin of mice using Silk and gCellulose films; suture and skin glue have been used as the control groups; the healing process at day 0, day 1 and day 2 for each group has been demonstrated in the figures.
Figure 10:
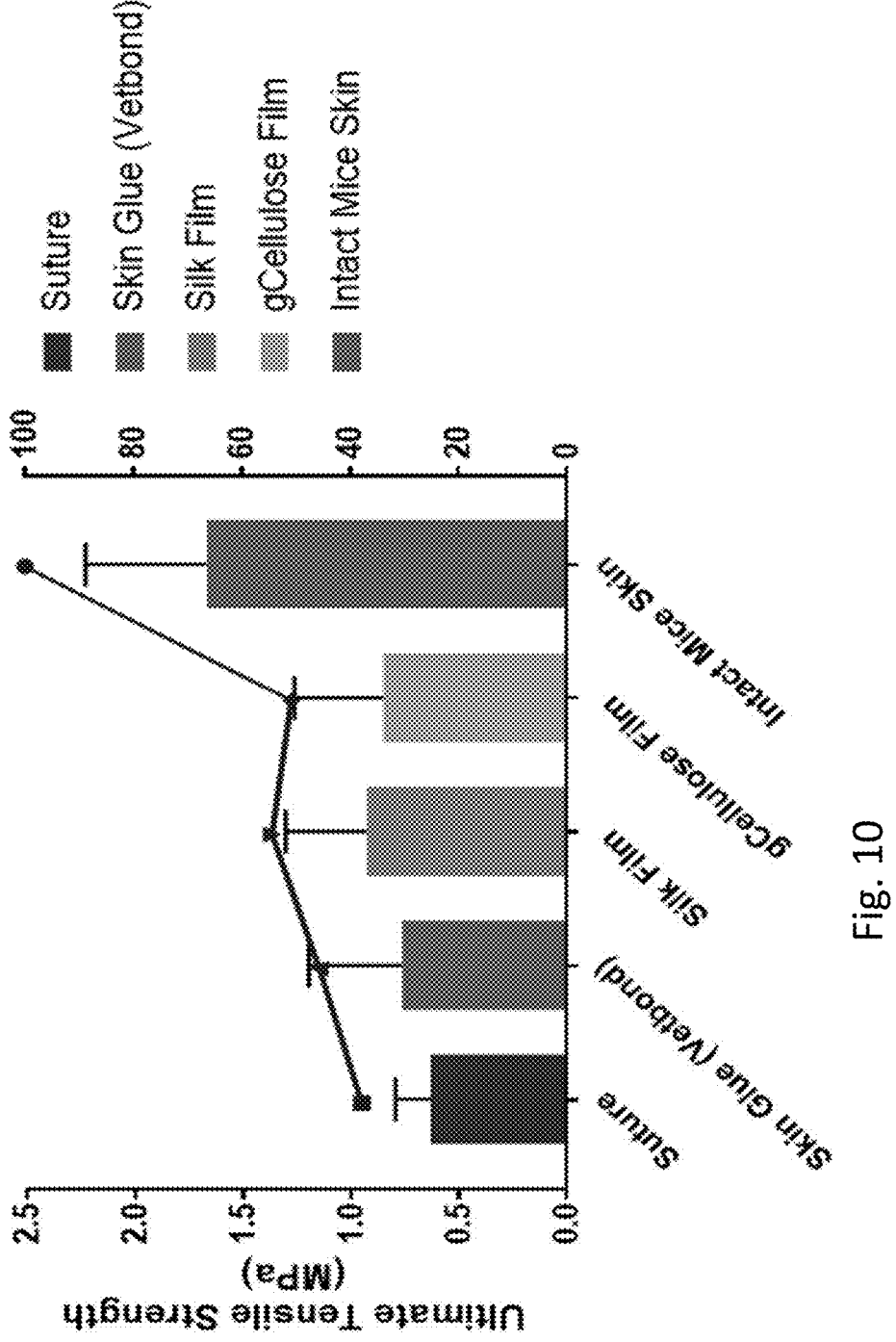
FIG. 10 shows a graph of the ultimate tensile strength of each group after 2 days. The right y axis shows the amount of recovery in tensile strength after 2 days for each group.

FIG. 9A shows healing on day 0, day 1, and day 2 with a suture for comparison purpose. FIG. 9B shows healing on day 0, day 1, and day 2 with silk film. FIG. 9C shows healing on day 0, day 1, and day 2 with a common glue. FIG. 9D shows healing on day 0, day 1, and day 2 with gCellulose film. By comparison, it appears that both the silk and gCellulose films enhanced healing over the common suture or glue.

FIG. 2 includes a graph that shows the ultimate tensile strength of each group after 2 days. The right y axis shows the amount of recovery in tensile strength after 2 days for each group.

Figure 11:
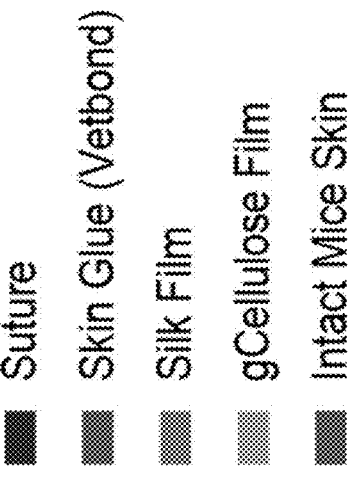
FIG. 11 shows the maximum strength of each group after 2 days.
Figure 11:
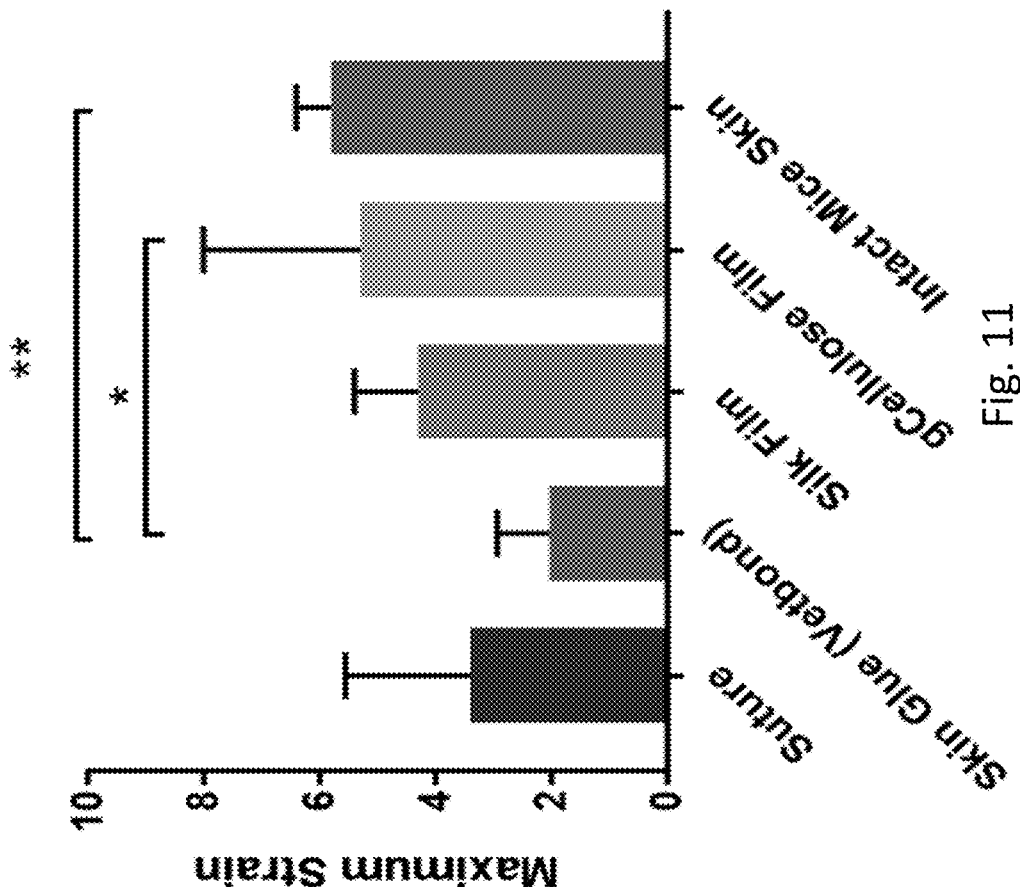

FIG. 11 shows the maximum strength of each group after 2 days.

One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

REFERENCES

Bouten, P. J. M., et al., The chemistry of tissue adhesive materials. Progress in Polymer Science, 2014. 39(7): p. 1375-1405.

Lloyd, J. D., M. J. Marque, and R. F. Kacprowicz, Closure techniques. Emergency Medicine Clinics of North America, 2007. 25(1): p. 73.

Annabi, N., et al., Elastic sealants for surgical applications. Eur J Pharm Biopharm, 2015. 95(Pt A): p. 27-39.

Bass, L. S. and M. R. Treat, Laser tissue welding: a comprehensive review of current and future clinical applications. Lasers Surg Med, 1995. 17(4): p. 315-49.

Talmor, M., Clifford B. Bleustein, and Dix P. Poppas., laser tissue welding: a biotechnological advance for the future. Archives of facial plastic surgery, 2001. 3: p. 207-213.

Russell Urie, S. Q., Michael Jaffe, and Kaushal Rege., Gold Nanorod-Collagen Nanocomposites as Photothermal Nanosolders for Laser Welding of Ruptured Porcine Intestines. ACS Biomater. Sci. Eng, 2015. 1: p. 805-815.

Boonkaew, B., et al., Antimicrobial efficacy of a novel silver hydrogel dressing compared to two common silver burn wound dressings: Acticoat and PolyMem Silver®. Burns, 2014. 40(1): p. 89-96.

Abdelgawad, A. M., S. M. Hudson, and O. J. Rojas, Antimicrobial wound dressing nanofiber mats from multicomponent (chitosan/silver-NPs/polyvinyl alcohol) systems. Carbohydr Polym, 2014. 100: p. 166-78.

Xie, J., et al., Silver nanoplates: from biological to biomimetic synthesis. ACS Nano, 2007. 1(5): p. 429-39.

Urie, R., et al., Gold Nanorod-Collagen Nanocomposites as Photothermal Nanosolders for Laser Welding of Ruptured Porcine Intestines. ACS Biomaterials Science & Engineering, 2015. 1(9): p. 805-815.

This patent application cross-references U.S. application Ser. No. 15/855,682 filed Dec. 27, 2017 and U.S. Provisional Application No. 62/294,226 filed Feb. 11, 2016, which applications are incorporated herein by specific reference in their entirety.

The invention claimed is:

1. A method of closing an opening in a tissue comprising:
providing a light absorbing material;
wherein the light absorbing material is in the form of a liquid, a gel, a hydrogel, a paste, or a film;
wherein the light absorbing material comprises a light absorbing polymer;
wherein the light absorbing material comprises chitosan-glutaraldehyde, silk-glycerol, alginate-glycerol, or cellulose-glycerol;
wherein the light absorbing material is devoid of gold particles, nanoparticles, chromophores, and light absorbing dyes;
forming the opening in the tissue;
introducing the light absorbing material directly into the opening in the tissue;
irradiating the light absorbing material with at least one light source so as to increase a temperature of the light absorbing material, causing edges of the opening in the tissue to adhere to the light absorbing material and/or to each other;
modulating the power of the light source to modulate the temperature increase from the light; and
approximating the edges before, during, or after irradiating the light absorbing material;
wherein the tissue is a single tissue;
wherein the at least one light source comprises a mid-infrared laser light; and
wherein the mid-infrared laser light has a wavelength between 2 microns and 10 microns.

2. The method of claim 1, comprising manually holding the edges closer together for a time period between about 1 second and 1 minute.

3. The method of claim 1, wherein the opening in the tissue is between at least two different tissues.

4. The method of claim 1, wherein the temperature increase is sufficient to cause the light absorbing material to interact with the tissue so as to close the opening in the tissue so as to approximate the tissue.

5. The method of claim 1, wherein the light absorbing material further comprises a second material comprising a natural polymer material selected from structural tissue proteins, polysaccharides, extracellular matrix proteins, connective tissue proteins, glycoproteins, glycoaminoglycans, fibrous proteins, protein fibers, or combinations thereof.

6. The method of claim 1, wherein the light absorbing material further comprises a second material comprising a semi-natural polymer material derived from a natural polymer material selected from structural tissue proteins, polysaccharides, extracellular matrix proteins, connective tissue proteins, glycoproteins, glycoaminoglycans, fibrous proteins, protein fibers, or combinations thereof.

7. The method of claim 1, wherein the light absorbing material further comprises a second material comprising a synthetic polymer material selected from poly(lactic acid), poly(glycolic acid), poly(lactic-glycolic acid), poly(vinyl alcohol), polyamide, polyurethane, poly(ethylene oxide), polyglyconate, poly(glycolic-caprolactone), polypropylene, polyethylene, poly(hydroxyl acid), polyhydroxyalkanoate, polyanhydride, poly(orthocarbonate), polycarbonate, polyphosphonate, silicones (e.g., polysiloxanes, such as polydimethyulsiloxane (PDMS) or others), or combinations thereof.

8. The method of claim 1, wherein the light absorbing material further comprises a second material selected from a crosslinker, a photoinitiator, or a bioactive agent.

9. The method of claim 1, wherein the light absorbing material further comprises a second material selected from collagen, laminin, fibronectin, elastin, hyaluronic acid, fibrin, gelatin, agarose, poly(lactic acid), poly(glycolic acid), poly(lactic-glycolic acid), silicones, poly(vinyl alcohol), polyamide, polyurethane, polyethylene oxide, or combinations thereof.

10. The method of claim 1, wherein the adhered tissue has an ultimate tensile strength of at least 0.25 MPa.

11. The method of claim 1, wherein the step of introducing the light absorbing material into the opening in the tissue does not comprise providing a structural element with the light absorbing material.

12. A method of closing an opening in a tissue comprising:

providing a light absorbing material;

wherein the light absorbing material is in the form of a liquid, a gel, a hydrogel, a paste, or a film;

wherein the light absorbing material comprises a light absorbing polymer;

wherein the light absorbing material is devoid of gold particles, nanoparticles, chromophores, and light absorbing dyes;

forming the opening in the tissue;

introducing the light absorbing material directly into the opening in the tissue;

irradiating the light absorbing material with at least one light source so as to increase a temperature of the light absorbing material, causing edges of the opening in the tissue to adhere to the light absorbing material and/or to each other;

modulating the power of the light source to modulate the temperature increase from the light; and approximating the edges before, during, or after irradiating the light absorbing material;

wherein the tissue is a single tissue;

wherein the at least one light source comprises a mid-infrared laser light;

wherein the mid-infrared laser light has a wavelength between 5 microns and 7 microns;

wherein the light absorbing material comprises chitosan-glutaraldehyde, silk-glycerol, alginate-glycerol, or cellulose-glycerol; and wherein the light absorbing material comprises a photoinitiator.

\* \* \* \* \*